United States Patent [19]
Blumenfeld

[11] Patent Number: 5,515,161
[45] Date of Patent: May 7, 1996

[54] CALIBRATION DEVICE FOR FLUORESCENCE PHOTOMETERS

[75] Inventor: Walter Blumenfeld, Airville, Pa.

[73] Assignee: Becton Dickinson and Company, Franklin Lakes, N.J.

[21] Appl. No.: 271,325

[22] Filed: Jul. 6, 1994

[51] Int. Cl.$^6$ .................................................. G01J 3/30
[52] U.S. Cl. ........................ 356/317; 356/243; 250/252.1
[58] Field of Search .................................. 356/317, 318, 356/243; 250/252.1 A

[56] References Cited

U.S. PATENT DOCUMENTS 4,681,444  7/1987  Ferber et al. ............................ 356/318

Primary Examiner—Vincent P. McGraw
Assistant Examiner—K. P. Hantis
Attorney, Agent, or Firm—Alan W. Fiedler

[57] ABSTRACT

A calibration device is disclosed for use with fluorescence photometers of the type which direct an excitation radiation at a sample to be tested, and then read the fluorescent emission from the sample to identify bacterial growth in the sample. In the past the emission reading accuracy of fluorescence photometers has been tested by passive standards. The known standards have some shortcomings, in that they may have varying characteristics with time and temperature, and further because they are difficult to manufacture without experiencing some variation between the standards. The present invention addresses the problem by generating a particular fluorescent emission and directing that emission towards a photometer to be tested. Since the emission which is directed outwardly of the calibration device is predetermined and known, this directed radiation can be compared to that which is read by the fluorescence photometer. In this way, a positive evaluation of the reading accuracy of the photometer can be made. In further embodiments of this invention, a second circuit is included in the calibration device for reading the excitation radiation from the photometer. The excitation radiation, as read, can be compared to that which the photometer was expected to generate. The emission radiation characteristics can be generated dependent upon the excitation radiation, or can be a fixed amount.

11 Claims, 2 Drawing Sheets

CALIBRATION DEVICE FOR FLUORESCENCE PHOTOMETERS

BACKGROUND OF THE INVENTION

This invention relates to a calibration device capable of generating a predetermined fluorescent emission, and then directing that emission towards a fluorescence photometer. By comparing the fluorescent emission read by the photometer with the actual emission from the calibration device, a determination can be made as to whether the photometer is accurately reading fluorescent emissions.

Fluorescence photometers are utilized in the evaluation of biological fluid samples. As one example, a body fluid sample, such as blood, may be placed with a culture medium in a test tube, along with a fluorescent chemical sensor responsive to biological activity. Known methods are utilized for directing an excitation radiation into the sample, and then reading the fluorescent emission from that sample. By comparing the emission to expected values, a determination can be made of whether bacterial activity is ongoing in the sample being evaluated. For purposes of this application, a "Fluorescence photometer" would also include any instrumentation incorporating a fluorescence measuring subsystem.

One aspect of such photometers is that they must be properly calibrated to be effective. If the photometer is not accurately reading the fluorescent emission, then the readings from that photometer will not provide accurate evaluations of the sample being tested. Thus, initial and periodic calibration must be performed on such photometers.

In the prior art, passive fluorescent standards are utilized to test the accuracy of fluorescence photometers. Such fluorescent standards may be a standard object, including a solid compound having known fluorescent properties. Other types of passive fluorescence standards are provided by liquid chemical compounds meant to approximate particular fluorescent characteristics of biological or chemical samples to be tested. These liquid or "fresh chemical" standards are subject to formulation problems and lot-to-lot variations.

For either type of passive standard, problems exist due to different responses by the standard to temperature, irreversible degradation with heat or time, and bleaching with repeated exposure to light (as could be caused by the excitation radiation directed from the fluorescent photometer). When the standard has characteristics that are different than expected, from its specified or tabulated values, incorrect readings will result at the photometer. An operator may then determine that a properly calibrated photometer requires adjustment or repair when, in fact, it is the standard which caused the inaccurate result.

Moreover, the evaluation of the fluorescent emission from such standards is necessarily compared to what is believed to be the excitation radiation generated by the fluorescence photometer under test. If the excitation radiation is out of tolerance (such as when it is the excitation portion of the photometer which requires adjustment), typical passive fluorescent standards may result in an indication that a properly calibrated photometer is improperly calibrated. That is, if the excitation radiation is different from specification, then the fluorescent radiation emitted by the standard will also be different than expected. The fluorescent photometer may accurately read the actual fluorescent emission, but could be identified as being "out of calibration," when in fact the excitation radiation is actually out of tolerance.

These various drawbacks with the use of fluorescent standards create difficulties in calibrating, repairing, manufacturing, and testing photometers.

SUMMARY OF THE INVENTION

The instant invention discloses a calibration device embodying structure capable of generating a predetermined fluorescent emission. That fluorescent emission is directed at a fluorescent photometer to be tested or calibrated. The fluorescent emission read by the photometer is compared to that which has actually been generated by the calibration device. If necessary, calibration of the photometer may then be performed. Since the calibration device generates a known fluorescent emission, the problems described above with regard to passive fluorescent standards are not encountered.

In a preferred embodiment of this invention, the calibration device also includes a circuit for receiving and reading an excitation radiation from the fluorescence photometer. The calibration device may generate a fluorescent emission that is proportionally dependent on the excitation radiation which has been read. Alternatively, the calibration device may be used in a "fixed" mode wherein the fluorescent radiation is generated independent of the excitation radiation that has been read. The proportional mode best approximates the "real world" where it is the excitation radiation which generates the emission; the fixed mode is useful for performing calibration of a fluorescence photometer's emission detector signals.

In a preferred embodiment of this invention, meters are associated with the calibration device for reporting the excitation radiation which is read from the fluorescence photometer, and also for reporting the generated fluorescent emission being directed at the photometer.

In one preferred embodiment of this invention, an optical head utilized in the calibration device includes a photodiode for receiving the excitation radiation from the fluorescence photometer, and transmitting electrical current corresponding to that radiation to a circuit for reading the excitation radiation. The optical head also preferably includes a plurality of light emitting diodes connected to an emission circuit for generating the emission radiation described above. In one embodiment of this invention, the optical head is cylindrical with the photodiode at a central axis, and the light emitting diodes are located on the circumference of a circle centered on the photodiode. In a second embodiment of this invention, the optical head has a series of rectangular faces, with the excitation radiation axis passing through one face to a photodiode, and the light emitting diodes directing their emission radiation through a second face. It should be understood that the geometry of the optical head may be varied to correspond to the fluorescent photometer to be tested.

In a method according to the present invention, a fluorescence photometer to be tested is positioned adjacent to the calibration device. The calibration device is preferably inserted into the sample holder of the photometer. An emission radiation having predetermined characteristics is generated in the calibration device, and is then directed toward the photometer. Characteristics of the generated emission are "reported" by being displayed on a meter. The photometer reads the fluorescent emission, and the emission read by the photometer is compared to the generated value. In this way, a determination is made of whether calibration or repair of the photometer is necessary. In further features of the method of this invention, the calibration device may also read the excitation radiation from the photometer, and may generate the emission radiation dependent on the excitation radiation that is read. Alternatively, the generated emission radiation may be fixed and independent of the excitation radiation which is read.

These and other features of the present invention can be best understood from the following specifications and drawings, of which the following is a brief description.

DETAILED DESCRIPTION OF A PREFERRED EMBODIMENT

Figure 1:
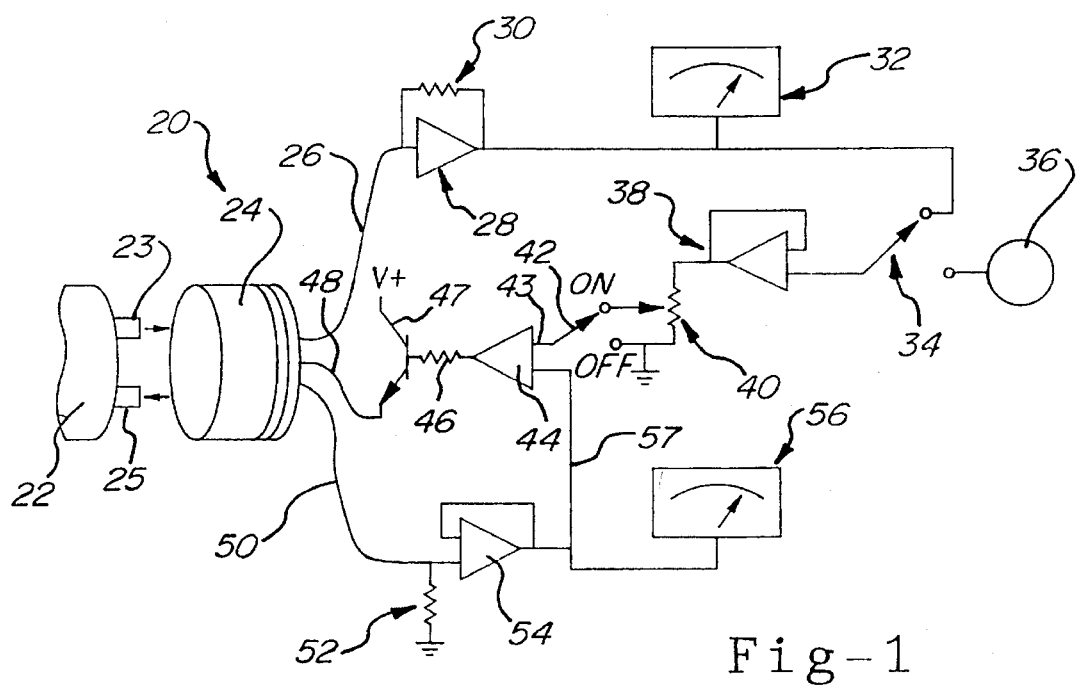
FIG. 1 is a partially schematic view of a first calibration device according to the present invention.

FIG. 1 shows a calibration device 20 for use with a fluorescence photometer 22. Fluorescence photometer 22 is shown schematically having a first assembly 23 for directing excitation radiation outwardly, and a second assembly 25 for receiving a return fluorescent emission from a sample. It should be understood that photometer 22 is as known in the art, and the details of this photometer and its operation form no portion of this invention.

An optical head 24 is positioned adjacent to photometer 22, and includes elements for reading the excitation radiation from photometer 23, and for generating a fluorescent emission to be directed at photometer 22. The optical head 24 is connected to the other portions of calibration device 20, which include circuits to read the excitation radiation from the photometer, and a circuit for generating an emission radiation and controlling the optical head 24 to direct that radiation toward the photometer to be tested. The "read" excitation radiation and the generated emission radiation are "reported" or displayed at the calibration device. Although the following circuits disclose embodiments for reading and generating the respective emissions, it should be understood that the details of the circuitry can vary in devices within the scope of this invention.

An excitation circuit 26 includes a transimpedance amplifier 28, converting the energy received from optical head into an analog voltage signal. A feedback resistor 30 is included to control scaling of the voltage signal. An excitation meter 32 displays the excitation radiation read from the photometer 22.

A mode switch 34 selectively connects the excitation circuit 26 to the emission-generating circuit, when it is desired to generate a fluorescent emission that is "proportional" or dependent on the excitation radiation that is read. This proportional mode simulates the "real world" where it is the excitation radiation that generates the emission. In the disclosed embodiment, it is the intensity of the emission radiation that is controlled. In the "proportional" mode, the generated emission is thus based on a proportion of the excitation radiation read from photometer 22.

Alternatively, a reference voltage 36 may be connected to the emission circuitry by mode switch 34 in a "fixed" mode. Although this mode is described as "fixed," it should be understood that the reference voltage 36 itself may be varied to test the photometer across a range of voltages.

The emission control signal leading to the emission circuit is buffered by amplifier 38. A scale factor potentiometer 40 is placed in line for adjusting the scaling of the emission control voltage. An on/off activation switch 42 may be operated to turn the emission circuitry on and off. The emission control voltage passes into line 43, and into the positive input of a difference amplifier 44. A base resistor 46 connects the output of difference amplifier 44 to a series pass transistor 47. The emitter output current of transistor 47 is directed into a line 48 leading to elements in optical head 24 for generating a fluorescent emission. A current return line 50 leads from optical head 24 and to a series resistor 52 connected to ground. A voltage thus develops in resistor 52. High impedance buffer amplifier 54 senses this voltage and drives fluorescent emission meter 56 for "reporting" or displaying the generated emission. An operator can compare the report displayed on the meter with the reading at the photometer to determine manually whether adjustment or repair of the photometer is necessary. A feedback line 57 from this voltage signal is connected to the negative input of the difference amplifier 44 to internally monitor the "reported" emission and to thereby provide the difference signal for control of the generated emission.

Figure 2:
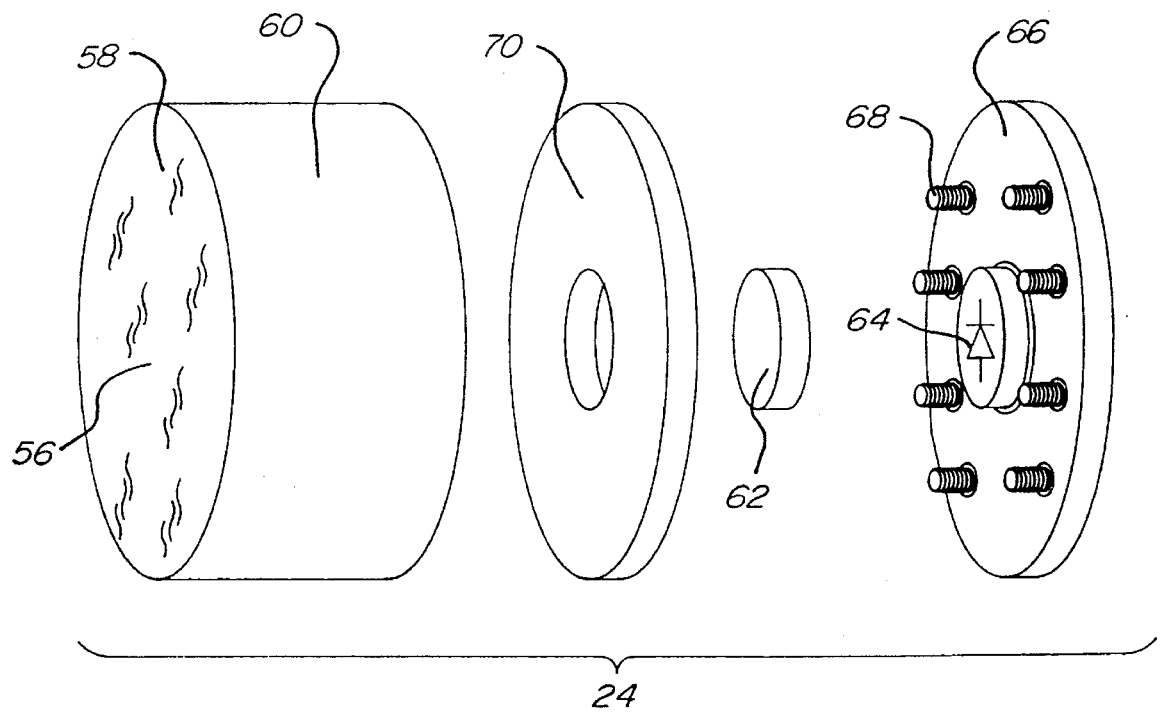
FIG. 2 is a first embodiment optical head that may be incorporated into the inventive calibration device.

As shown in FIG. 2, optical head 24 includes an active area around optical axis 56 centered at the front surface of a cylindrical diffuser 58. Diffuser 58 is located at the front end of optical head housing 60. An excitation filter 62 is placed on optical axis 56 in front of a photodiode 64. Photodiode 64 is mounted on an opaque backplate 66. A series of LEDs 68 are mounted circumferentially spaced about optical axis 56. Emission filter 70 is placed in front of LEDs 68. LEDs 68 are driven by the emission circuit through line 48, while photodiode 64 is connected to the excitation circuit through line 26.

In operation, when one desires to test photometer 22, the excitation radiation leaving photometer 22 passes through cylindrical diffuser 58, excitation filter 62, into photodiode 64, into line 26, and is then displayed on meter 32. In the "proportional" mode, the excitation radiation which is read is connected through mode switch 34 to control the voltage control at line 43. In either of the "proportional" or "fixed" modes, a fluorescent emission is determined and a signal passes through line 48 to generate an emission from LEDs 68 as desired.

The radiation leaving LEDs 68 passes through filter 70 and then outwardly of cylindrical diffuser 58. The emission is distributed uniformly about the circumference of the cylindrical diffuser 58. In a preferred embodiment it is the intensity of the emission which is selected to be generated, and which is read by the photometer. The generated emission is displayed or "reported" at meter 56. The reported emission is compared to that read by the photometer 22 to determine the accuracy of the photometer. Of course, a worker in the art would realize that the property to be controlled in the generated emission would be the property which is read by the particular photometer and that properties other than intensities may be utilized within the scope of this invention. Examples of other properties include time-domain measurements, such as phase-resolved or relative modulation ratio techniques.

Figure 3:
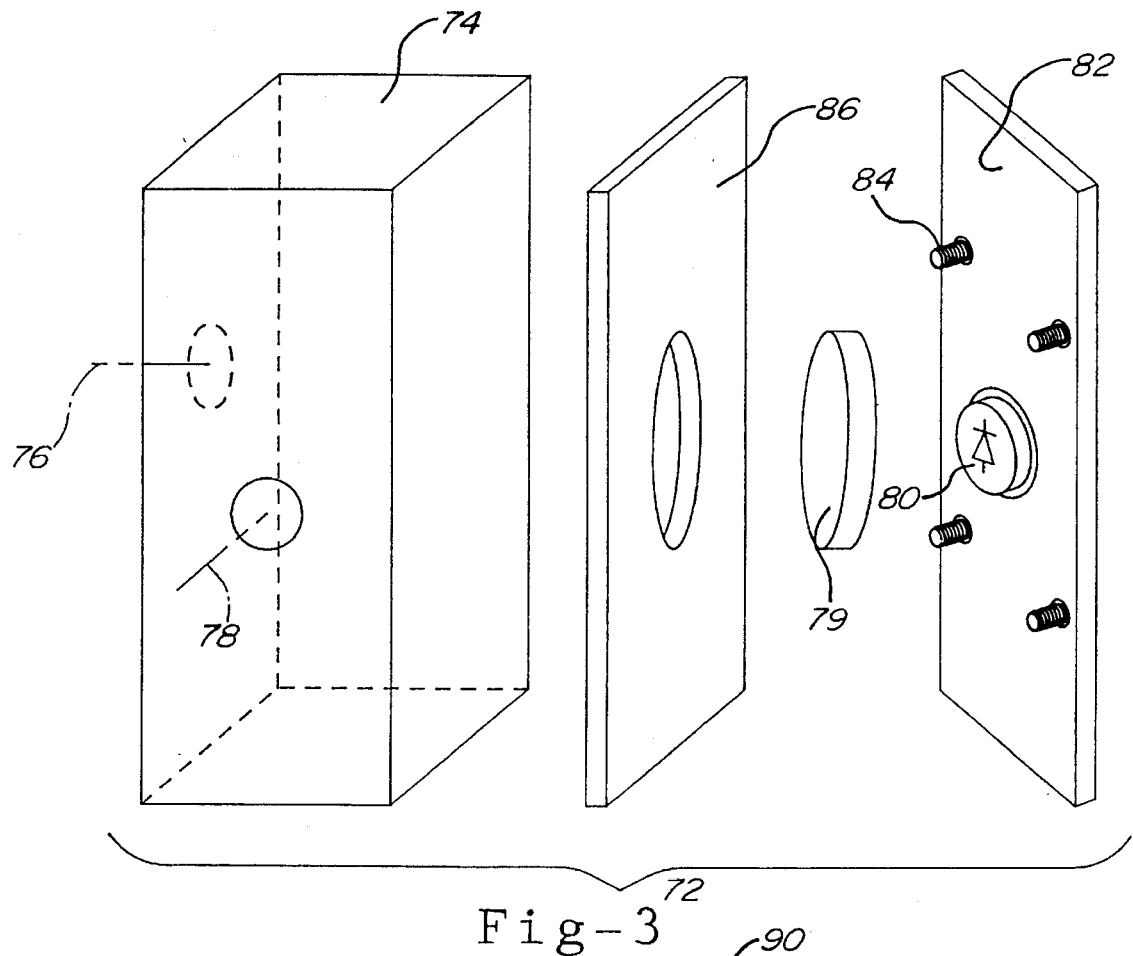
FIG. 3 is a second embodiment optical head that may be incorporated into the inventive calibration device.

An alternative optical head 72 is illustrated in FIG. 3. The excitation axis 78 and the emission axis 76 extend through spaced rectangular faces of the body 74 of optical head 72. Photodiode 80 is mounted on plate 82, as are LEDs 84. An emission filter 86 is also included. The optical structure in optical head 72 is as shown in FIG. 2, however, the operative members are aligned with the respective axes, as shown. By comparing FIGS. 2 and 3 it is apparent that the present invention will allow modification of the optical head to correspond to the geometry required by a particular photometer to be tested.

Figure 4:
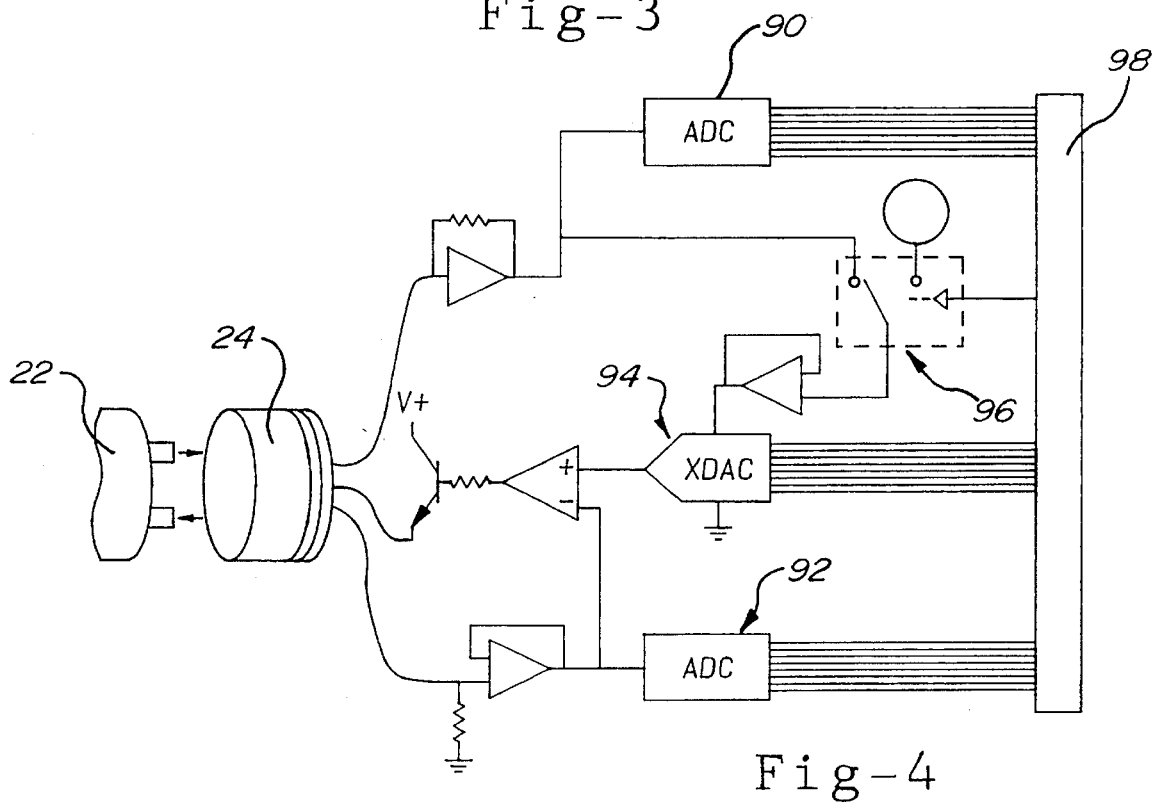
FIG. 4 is a second embodiment calibration device according to the present invention.

FIG. 4 shows an automated microprocessor-controlled calibration system 89. The meter readouts as shown in the FIG. 1 embodiment are replaced by analog to digital converters 90 and 92. The converters 90 and 92 "report" through microprocessor bus interface 98. The mode switch is replaced by a solid state relay 96. The on/off enabling switch and the scale factor potentiometer from the first embodiment are replaced by a digital to analog converter 94. All of the control and data reporting, display or readout functions are software controlled via a microprocessor bus interface 98.

In both embodiments, both the read and generated radiations are reported in some way. The characteristic of the radiation both read and generated at the calibration device must be compared to those at the photometer. The characteristic of the excitation radiation which is read at the calibration device must be compared to the characteristics of the excitation radiation that was expected from the photometer. If the two differ, the photometer should be adjusted, repaired or calibrated. Similarly, the characteristics of the emission radiation which has been directed from the calibration device must be compared to that which is actually read by the photometer. Again, adjustment is necessary if the two differ. Although no direct connection between the photometer and the calibration device is disclosed, it may be preferable to electrically connect the two such that the reported emission from the calibration device can be compared to the readings at the photometer and an indication can be made as to whether adjustment is necessary. Although two embodiments of "reporting" systems are disclosed, it should be understood that other ways of "reporting" and comparing the generated emission and that read by the photometer would be apparent to a worker in the art.

The present invention thus provides a simple, nondegradable, temperature insensitive calibration device which eliminates the variations that were experienced by the prior art standards. The inventive calibration device can be utilized in quality control or in the manufacture of fluorescence instruments, diagnostics and repair work, and in any application where it is desirable to test the accuracy of a particular photometer. The inventive calibration device may be utilized as an standalone tool or could be embedded into an instrument as a self-testing subsystem.

Although preferred embodiments of the present invention have been disclosed, a worker of ordinary skill in the art would recognize that certain modifications would come within the scope of this invention. For that reason, the following claims should be studied in order to determine the true scope and content of this invention.

I claim:

1. A calibration device for testing and calibrating a fluorescence photometer having a first assembly for directing an excitation radiation to a sample and a second assembly for receiving a return fluorescent emission from the sample, said calibration device comprising:

means to read an excitation radiation received from a first assembly of a photometer to be tested;

means to display to an operator said excitation radiation that has been read;

means for generating an emission radiation that is a predetermined proportion of said excitation radiation;

means to display to the operator said generated emission radiation; and means for directing said generated emission radiation at a second assembly of the photometer to be tested to thereby test and calibrate the first and second assembly of the photometer to be tested.

2. A calibration device as recited in claim 1, further including a switch for selectively connecting said means for generating to a control signal source independent of the excitation radiation read by said means to read, or selectively connecting said means for generating to said means to read such that the characteristics of the generated emission radiation are dependent on the excitation radiation read by said means to read.

3. A calibration device as recited in claim 1, wherein said calibration device includes an optical head including a photodiode for reading the excitation radiation from the photometer to be tested, and further including radiation-generating members for generating the emission radiation.

4. A calibration device as recited in claim 3, wherein said photodiode is mounted on a central axis on said optical head, and the radiation-generating members are positioned circumferentially spaced about said central axis.

5. A calibration device as recited in claim 1, wherein the intensity of said emission is a reported characteristic.

6. A calibration device as recited in claim 1, wherein an optical head is incorporated into said calibration device, said optical head including:

said means to read said excitation radiation from said photometer; and generating members including said means for generating said emission radiation, and said means for directing said generated emission radiation towards the photometer to be tested.

7. A calibration device as recited in claim 6, wherein reading means is a photodiode located on a central axis of said optical head, and operable to receive excitation radiation from the photometer to be tested, said generating members including a plurality of radiation generating members positioned about said photodiode and connected to appropriate circuitry for generating said emission radiation, and directing said emission radiation outwardly of said optical head.

8. A calibration device as recited in claim 7, wherein said generating members are light-emitting diodes.

9. A calibration device as recited in claim 7, wherein said optical head has a plurality of faces, and said excitation radiation is directed towards said photodiode through one of said plurality of faces, said emission radiation being directed from said generating members outwardly of said optical head through a second of said plurality of faces.

10. A calibration device as recited in claim 1, wherein each of said display means is a meter providing a visual display.

11. A method of testing a fluorescence photometer having a first assembly for directing an excitation radiation to a sample and a second assembly for receiving a return fluorescent emission from the sample, said method comprising the steps of:

generating an excitation radiation in a first assembly of the photometer to be tested;

directing said excitation radiation at a calibration device;

reading said excitation radiation at said calibration device;

generating within said calibration device an emission radiation that is a predetermined proportion of said read excitation radiation;

directing said generated emission radiation out of said calibration device and at a second assembly of the photometer to be tested;

reading said generated emission radiation at the second assembly of the photometer to be tested; and comparing said generated emission radiation read by the second assembly with said emission radiation generated by said calibration device to thereby test the first and second assembly of the photometer to be tested.

* * * * *